United States Patent [19]

Wan

[11] 4,241,219

[45] Dec. 23, 1980

[54] TREATMENT OF CARBONYLATION EFFLUENT

[75] Inventor: Chee-Gen Wan, North Brunswick, N.J.

[73] Assignee: Halcon Research and Development Corp., New York, N.Y.

[21] Appl. No.: 61,712

[22] Filed: Jul. 30, 1979

[51] Int. Cl.³ .............................................. C07C 51/12
[52] U.S. Cl. .................................... 560/232; 562/517; 260/544 A; 260/544 Y; 260/546; 260/549; 570/263; 423/500; 560/248; 570/263
[58] Field of Search ............... 260/544 A, 544 Y, 546, 260/549, 652 P; 560/232, 248; 562/517, 519; 423/500

[56] References Cited

U.S. PATENT DOCUMENTS

| 3,816,490 | 6/1974 | Forster et al. ...................... 260/413 |
| 3,887,595 | 6/1975 | Nozaki ............................... 260/410.6 |
| 4,115,444 | 9/1978 | Rizkalla ............................... 260/549 |
| 4,121,978 | 10/1978 | Becuwe ................................. 203/58 |
| 4,134,912 | 1/1979 | Naglieri et al. ..................... 562/579 |

Primary Examiner—Robert Gerstl
Attorney, Agent, or Firm—William C. Long; David Dick; Riggs T. Stewart

[57] ABSTRACT

In the carbonylation of esters and/or ethers the reaction mixture is separated into fractions to recover components therefrom, gases are withdrawn from the system and halogen values are recovered from said gases by contact with a component recovered from said reaction mixture.

5 Claims, 1 Drawing Figure

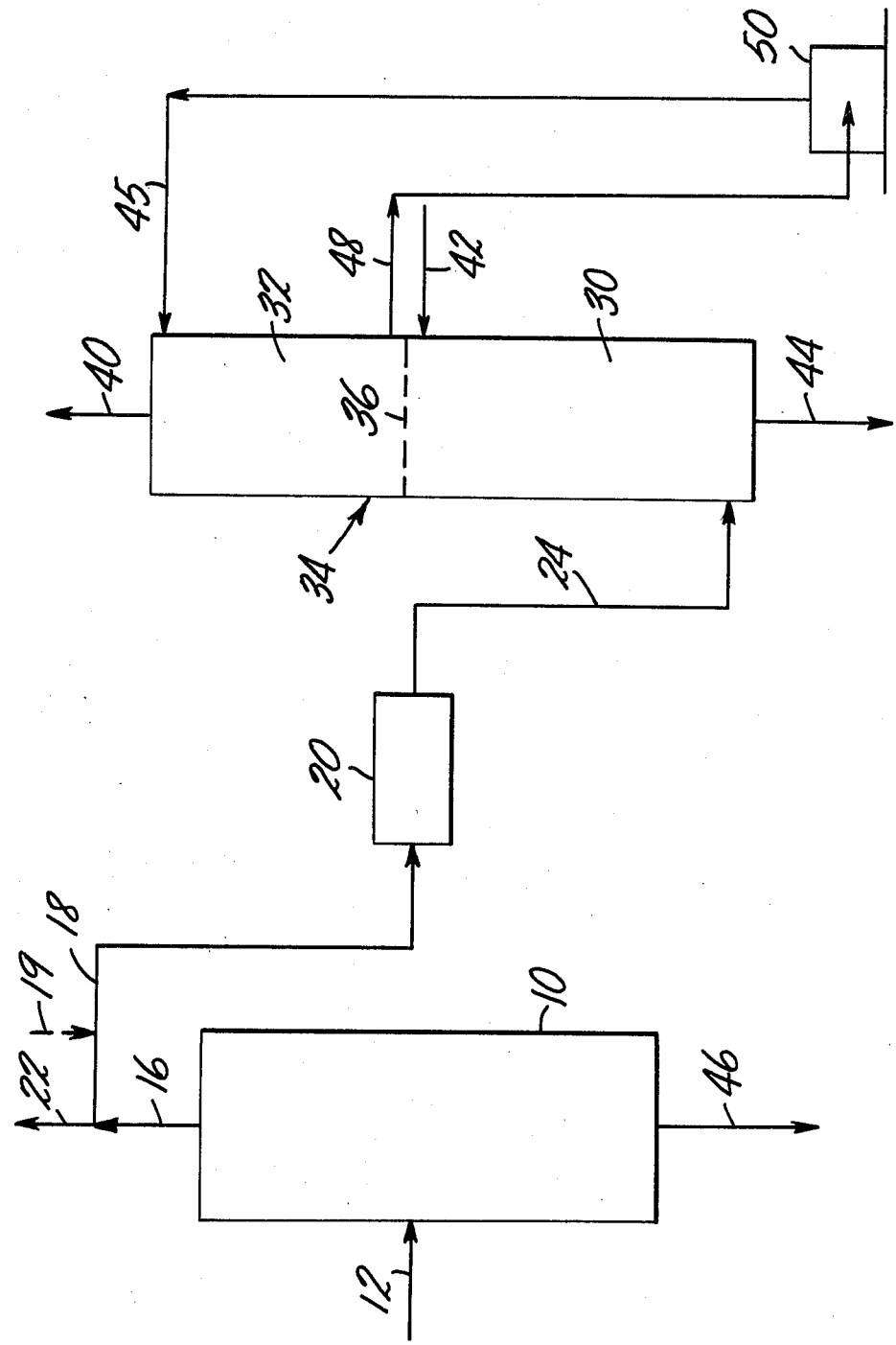

TREATMENT OF CARBONYLATION EFFLUENT

This invention relates to the carbonylation of esters and/or ethers to produce various carbonylation products, and is more particularly concerned with the carbonylation of methyl acetate and/or dimethyl ether to produce a carbonylation product comprising acetic anhydride and other carbonylation products.

Acetic anhydride has been known as an industrial chemical for many years and large amounts are used in the manufacture of cellulose acetate. It has commonly been produced on an industrial scale by the reaction of ketene and acetic acid. It is also known that acetic anhydride can be produced by the decomposition of ethylidene diacetate, as well as by the oxidation of acetaldehyde, for example. Each of these "classic" processes has well-known drawbacks and disadvantages and the search for an improved process for the production of acetic anhydride has been a continuing one. Proposals for producing anhydrides by the reaction of carbon monoxide upon various reactants (carbonylation) have been described, for example, in Reppe et al. U.S. Pat. Nos. 2,729,561, 2,730,546 and 2,789,137, using cobalt or nickel catalysts under very high pressure. More recently, carbonylation at lower pressures has been proposed in processes employing Group VIII noble metal catalysts with and without promoters. Processes of this type are disclosed in Lapporte et al. U.S. Pat. No. 3,927,078 and in Kuckertz U.S. Pat. No. 4,046,807. Particularly attractive processes for preparing carboxylic acid anhydrides, including acetic anhydride, by the carbonylation of methyl acetate are disclosed in British Patent No. 1,468,940 which is based on copending U.S. applications of Colin Hewlett Ser. No. 394,220, filed Sept. 4, 1973 and Ser. No. 467,977, filed May 8, 1974, and in U.S. Pat. No. 4,115,444 of Sept. 19, 1978. Belgian Patent No. 839,321 which is the counter-part of U.S. application Ser. No. 654,662 filed Feb. 5, 1976, discloses a process for the carbonylation of methyl acetate wherein the carbonylation is carried out in the presence of substantial amounts of hydrogen so that the acetic anhydride formed is accompanied by ethylidene diacetate, acetaldehyde and acetic acid. The disclosures of said British and Belgian patents, and said U.S. Pat. No. 4,115,444 are incorporated herein by reference.

Such carbonylations are carried out in the presence of Group VIII noble metals, i.e., rhodium, iridium, platinum, palladium, osmium and ruthenium, and their compounds, with or without inorganic and/or organic promoters, and the carbonylation system contains halogen moieties, especially bromine or iodine moieties, which may be introduced in the form of organic halides, such as a methyl halide, e.g., methyl iodide, or an acyl halide, such as acetyl iodide, or in the form of other organic halides or as the hydro-halide or other halide, e.g., salts, such as the alkali metal or other metal salts, or even as the elemental halogen, such as elemental iodine or bromine. The halogen moieties interact in the system and appreciable quantities of these halogen values become a part of the gaseous phase in the carbonylation reaction zone. This gaseous phase is bled from the system, particularly in continuous operation in order to prevent the buildup of undesired components, e.g., diluent gases or light by-product compounds, such as methane, and this bleed stream contains halogen values which exist in the vapor phase. Loss of these values by discarding the bleed stream represents a significant waste and is disadvantageous from various standpoints, including economic considerations. Moreover, they contaminate the bleed stream and cause problems with respect to discarding the stream or using its components having fuel and chemical values, such as methane. It is, therefore, important to recover these halogen values so that they can be returned to the carbonylation system and so that a purified bleed stream can be discharged. This, however, has not heretofore been an easy task. The halogen values generally exist in the form of methyl iodide, ethyl iodide, acetyl iodide and the like, with the principal halogen values being in the form of methyl iodide.

It is accordingly an object of this invention to provide a process for the recovery of halogen values from gaseous streams derived from carbonylation reactions.

In accordance with the invention, it has been surprisingly discovered that the halogen values, particularly iodine values, can be effectively and efficiently recovered from gaseous streams resulting from the carbonylation of methyl acetate and/or dimethyl ether employing Group VIII noble metals and halogen moieties by bringing such gaseous streams into direct counter-current contact with a stream of one or more of the carbonylation products having boiling points above 100° C., particularly acetic anhydride, ethylidene diacetate, acetic acid, or mixtures containing them. Thus, in accordance with the invention, a gaseous stream containing halogen values is "scrubbed" with a high boiling but volatilizable product of the carbonylation reaction which produced the gaseous stream being purified.

The scrubbing of the gaseous stream in accordance with the invention will effectively remove essentially all of the halogen values and will also remove any volatile organic components of the carbonylation reaction system which may be entrained or otherwise present in the gaseous stream, such as methyl acetate. These organic components will be present in relatively small amounts but their recovery is nevertheless desirable and it is one of the features of the process of this invention that not only the halogen values are recovered but other valuable components are removed as well. Furthermore, the gas stream being treated not only contains diluent gases along with carbon monoxide and hydrogen but also contain by-product gases, such as the above-mentioned methane, and the gas stream after treatment is in a highly purified form and can be directly vented without problem or can be used as fuel.

Advantageously, the gaseous effluent from the scrubbing zone is given a final or "clean-up" treatment to eliminate any residual iodine values, usually in amounts expressed in parts per million, which may be present. The liquid stream containing the halogen values, as well as organic components such as methyl acetate, can be combined with the feed to the carbonylation reaction so that the halogen values and methyl acetate can be used for further carbonylation. Thus, following its passage through the scrubbing zone, the scrubbing liquid, e.g., acetic anhydride, containing the recovered halogen values and organic values is conveniently sent to the carbonylation zone wherein the recovered halogen values can again participate in the carbonylation along with any recovered methyl acetate and other organic components. Because the scrubbing liquid is indigenous to the carbonylation system, it can be introduced directly into the carbonylation zone and does not create the problems which would arise if a "foreign" scrubbing liquid were used. A foreign scrubbing liquid would require additional steps to free the halogen and other values from it since its introduction into the carbonylation zone could cause a serious upset to the reaction. There is thus provided an efficient, effective, self-contained purification system which is integrated with the carbonylation reaction and which makes possible the recovery of valuable components useful in the carbonylation reaction which would otherwise be lost and would contaminate the purge gases so that they could not be vented or used without causing problems.

A fuller understanding of the invention will be obtained by reference to the accompanying drawing wherein there is shown, entirely diagrammatically, a system for carrying out the process of the invention.

Referring to the drawing, the reference numerial 10 designates a vapor-liquid separation zone which receives via line 12 a stream obtained from the carbonylation reaction of methyl acetate and/or dimethyl ether in the presence of a Group VIII metal and in the presence of halogen moieties such as methyl iodide or methyl bromide. Suitably, the stream is at a temperature in the range of about 0° to 150° C., preferably 30° to 80° C. Separation zone 10, which can be in the form of a drum or other like vessel, is maintained at a pressure within the range of 20 to 1,000 psia, preferably 50 to 500 psia. The stream entering through line 12 is separated in separation zone 10 into liquid and gaseous portions, the gaseous portion containing those components which are not condensable at ordinary temperatures and pressures. It is a gaseous mixture of this type which contains the volatile halogen values which are effectively recovered by the process of this invention. This gaseous stream is removed via line 16 and some or all of it is diverted via line 18 to a compressor 20. The remainder of the stream, if any, is withdrawn via line 22 and recycled to the carbonylation reactor (not shown). In compressor 20, the bleed or "purge" stream from line 18 is compressed to a pressure of 200 to 1500 psia, preferably 400 to 800 psia, and is fed via line 24 to primary scrubbing zone 30 which is conveniently in the form of a column 34 containing trays or packing to increase gas-liquid contact. In some cases, a gaseous purge stream may be removed directly from the carbonylation zone (not shown). Such a stream also may contain volatile halogen values and can be treated by the process of this invention and can be introduced directly into line 18, as indicated by the broken line at 19. In the embodiment illustrated in the drawing, scrubbing zone 30 forms the lower portion of a columm 34 but scrubbing zone 30 may be defined by a separate packed or tray column, if desired. A final or clean-up scrubbing zone 32 is defined in the upper portion of the vessel 34 and is separated from scrubbing zone, e.g., by a chimney tray, forming a partition allowing gas but not liquid to pass, as indicated diagrammatically by a broken line 36. The gaseous stream entering through line 24 passes upwardly through primary scrubbing zone 30 and thereafter passes upwardly through final scrubbing zone 32 and is removed via line 40. In the primary scrubbing zone 30, the gaseous mixture is brought into counter-current contact with a downwardly flowing stream of a scrubbing agent, which in accordance with the invention, is a product of the carbonylation of methyl acetate and/or dimethyl ether with carbon monoxide or carbon dioxide and hydrogen. Typically, this scrubbing liquid is acetic anhydride, although ethylidene diacetate, acetic acid, and the like may also be used. The scrubbing liquid enters scrubbing zone via line 42 and leaves via line 44 after having removed halogen values from the upwardly-flowing gaseous stream. In the scrubbing zone, the liquid-vapor relationship (L/V) is suitably 0.1 to 10, preferably 0.5 to 2. The liquid exiting at line 44 is recycled to the carbonylation zone (not shown), wherein its halogen values and the other values it may contain are reused in the carbonylation reaction. The scrubbing liquid entering line 42 is suitably a portion of the product mixture withdrawn from the carbonylation zone after it has been fractionally distilled to separate it into its component parts by ordinary fractional distillation, such as described in the above-mentioned U.S. Pat. No. 4,115,444. However, a scrubbing liquid of the character indicated, from an external source viz. indigenous to the carbonylation system, may be used, if desired. Similarly, it will be understood that the stream entering separation zone 10 via line 12 may be a combined stream representing the combination of effluents from more than one carbonylation reaction, e.g., a carbonylation with carbon monoxide alone and a carbonylation with carbon monoxide and hydrogen.

The halogen-value-containing streams which are treated in accordance with the invention can vary widely in their content of halogen values, e.g., depending upon the extent to which the separation in zone 10 is effected. Typically, although not necessarily, the content of halogen-containing compounds varies from about 1 to 15 mol percent of the total stream which typically also contains carbon monoxide and other gases such as hydrogen, methane and the like, as previously indicated, as well as organic components of the carbonylation reaction system such as methyl acetate. When the stream is obtained from a carbonylation using carbon monoxide and hydrogen, it will, of course, contain hydrogen. None of these components of the gaseous stream is, however, affected by passing through the scrubbing zones, but the halogen values and any organic values present can be essentially completely removed, so that the gases exiting via line 40 are essentially only the non-condensable components of the original stream fed via line 24.

As indicated above, the scrubbing zone in which the gaseous stream is treated in accordance with the invention to remove its halogen values is conveniently in the form of a column containing trays, or packing such as berle saddles, metal helices, Raschig rings and the like. Preferably, the column contains at least 10 theoretical plates and in general contains 10 to 30 theoretical plates but it will be understood that there is no upper limit on the number of theoretical plates which may be employed, other than economic considerations, as will be apparent to persons skilled in the art.

In the embodiment illustrated, there is shown a final or clean-up scrubbing zone 32 placed above scrubbing zone 30. The use of such a zone is optional, depending upon the final purity desired in the effluent gases. Thus, as seen in the drawing, from scrubbing zone 30 the upwardly flowing gas stream, after its contact with the downwardly flowing scrubbing liquid in zone 30, enters a final scrubbing zone 32 into which it comes into contact with a second scrubbing liquid stream. This scrubbing liquid can be of the same composition as the first scrubbing liquid referred to above in connection with zone 30 but it can be any high-boiling liquid in which the halogen values are soluble, such as glycol, and like high-boiling liquids or it can be a fluid which contains compounds which will react chemically with the halogen values, e.g., alkali metal hydroxides, such as sodium and potassium hydroxides, or alkali metal salts, especially carboxylates, such as sodium acetate, and like compounds. This second scrubbing liquid enters the upper portion of zone 32 via line 45 and is withdrawn from the lower portion of zone 32 through line 48. The second scrubbing liquid is maintained in a closed-circuit and is circulated via a pump 50. When the second scrubbing liquid in the circuit containing pump 50 has become saturated with halogen values or the chemical reagent has become exhausted, it is replaced. Alternatively, a purge of this circulating stream can be taken and the purge made up by replacing it with a fresh quantity of the second scrubbing liquid, as will be apparent to persons skilled in the art. The treated gaseous stream finally is withdrawn via line 40 which is connected to the top of zone 32. When, however, the second scrubbing zone 32 is not employed, vent line 40 will, of course, be connected directly to the upper portion of zone 30.

As previously mentioned, the gaseous stream which is treated in accordance with this invention is derived from the carbonylation of methyl acetate and/or dimethyl ether and is the gaseous portion separated from the reaction product of such a carbonylation. The carbonylation itself, however, forms no part of the present invention and representative carbonylations with Group VIII metals are described inter alia in the above-mentioned British Pat. No. 1,358,940, U.S. Pat. No. 4,115,444, Belgian Pat. No. 839,321 as well as in U.S. Pat. Nos. 4,002,677 and 4,002,678.

Thus, in a typical case, carbonylation of methyl acetate or dimethyl ether is carried out continuously in the presence of a Group VIII metal catalyst, especially a Group VIII noble metal catalyst, with or without the presence of a promoter, but in the presence of a halide such as methyl iodide. Volatile components of the reaction mixture are then continuously separated from the relatively non-volatile Group VIII metal catalyst and the latter is continuously reused for further carbonylation. Typically, although not necessarily, the carbonylation takes place in a carbonylation zone and separation takes place by means of a flash distillation under a pressure lower than that prevailing in the carbonylation zone. Heat can be added or removed or the flash distillation can be carried out adiabatically, as will be apparent to persons skilled in the art. An adiabatic flash distillation employed in connection with the preparation of acetic acid is disclosed in Eubanks et al. U.S. Pat. No. 3,845,121.

It is believed that a fuller understanding of the invention will result from a discussion of representative carbonylation reactions involving methyl acetate from which are obtained halogen value-containing gaseous streams for treatment in accordance with the invention.

Carbonylation involving methyl acetate and carbon monoxide is typically carried out at temperatures of 20° C. to 500° C., preferably 100° to 300° C. under a carbon monoxide partial pressure of 0.1 to 15,000 psi, and, as mentioned, is facilitated by the use of a catalyst, most suitably a Group VIII noble metal, i.e., rhodium, iridium, ruthenium, palladium, osmium and/or platinum, as disclosed in Belgain Pat. Nos. 819,455 and 839,321, and in U.S. Pat. No. 4,115,444. For ease of description, the invention will be described in terms of the carbonylation of methyl acetate. It will, of course, be understood that methyl acetate can be replaced or supplemented with dimethyl ether in the feed. It has been observed that the dimethyl ether is converted to methyl acetate in the carbonylation reaction so that it may be considered a methyl acetate precursor. When, therefore, reference is made to methyl acetate as a feed to the carbonylation, it will be understood that the dimethyl ether precursor is also contemplated. As previously indicated, the invention is also fully applicable to the carbonylation of other alkyl esters of alkanoic acids such as those described in U.S. Pat. No. 4,115,444, British Pat. No. 1,468,940 and Belgian Pat. No. 819,455.

The Group VIII metal carbonylation catalyst can be supplied and used in any convenient form, viz. in the zero valent state or in any higher valent form. For example, the catalyst may be the metal itself in finely-divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 atoms. Complexes of the metals can be employed, e.g., the metal carbonyls, such as iridium and rhodium carbonyls, e.g., hexarhodium hexadecacarbonyl, or as other complexes such as the carbonyl halides, e.g., iridium tri-carbonyl chloride $[Ir(Co)_3Cl]_2$ or chlorodicarbonyl rhodium dimer, or the acetylacetonates, e.g., rhodium acetylacetone $Rh(C_5H_7O_2)_3$. It will be understood that the foregoing compounds and complexes and classes of compounds and complexes are merely illustrative of suitable forms of the Group VIII metal catalyst and are not intended to be limiting.

The metal employed may contain impurities normally associated with the commercially available metal or metal compounds, and need not be purified any further. Thus, the commercially available metal or metal compound is suitably employed.

The amount of Group VIII metal catalyst is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, the catalyst is employed in the amount of 1 mol per 10 to 100,000 mols of ester, preferably 1 mol per 50 to 10,000 mols of ester, and most preferably 1 mol per 50 to 2,000 mols of ester.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like the other reactants, should, however, be essentially dry, i.e., the CO and the other reactants should be reasonably free from water. The presence of minor amounts of water such as may be found in the commercial forms of the reactants is, however, acceptable. Hydrogen, which may be present in very small (trace) amounts as an impurity, is not objectionable and may tend to stabilize the catalyst.

It has been previously found that the activity of the Group VIII noble metal catalysts described above can be significantly improved, particularly with respect to reaction rate and product concentration, by the concurrent use of a promoter. Effective promoters include the elements having atomic weights greater than 5 of Groups IA, IIA, IIIA, IVB, VIB, the non-noble metals of Group VIII and the metals of the lanthanide and actinide groups of the Periodic Table. Particularly preferred are the lower atomic weight metals of each of these groups, e.g., those having atomic weights lower than 100, and especially preferred are metals of Groups IA, IIA and IIIA as are metals of Group VIB and the non-noble metals of Group VIII. In general, the most suitable elements are lithium, magnesium, calcium, titanium, chromium, iron, nickel and aluminum. The particularly preferred elements are lithium and chromium. The promoters may be used in their elemental form, e.g., as finely-divided or powdered metals, or they may be employed as compounds of various types, both organic and inorganic, which are effective to introduce the element into the reaction system. Thus, typical compounds of the promoter elements include oxides, hydroxides, halides, e.g., bromides and iodides, oxyhalides, hydrides, alkoxides, and the like. Especially preferred organic compounds are the salts of organic mono-carboxylic acids, e.g., alkanoates such as acetates, butyrates, decanoates and laurates, benzoates, and the like. Other compounds include the metal alkyls, carbonyl compounds as well as chelates, association compounds and enol salts. Particularly preferred are the elemental forms, compounds which are bromides or iodides, and organic salts, e.g., salts of the monocarboxylic acid corresponding to the anhydride being produced. Mixtures of promoters can be used, if desired, especially mixtures of elements from different Groups of the Periodic Table. The exact mechanism of the effect of the promoter, or the exact form in which the promoter acts, is not known but it has been noted that when the promoter is added in elemental form, e.g., as a finely-divided metal, a slight induction period is observed.

The quantity of promoter can vary widely but preferably it is used in the amount of 0.0001 mol to 100 mols per mol of Group VIII noble metal catalyst, most preferably 0.001 to 10 mols per mol of catalyst.

In the working up of the reaction mixtures, e.g., by distillation, as discussed above, the promoter generally remains with the Group VIII metal catalyst, i.e., as one of the least volatile components, and is suitably recycled or otherwise handled along with the catalyst.

The activity of the Group VIII noble metal catalysts described above is also significantly improved, particularly with respect to reaction rate and product concentration, catalyst stability and corrosion inhibition, by the use of an organic promoter, and particularly advantageous is the concurrent use of a promoter combination or co-promoter system containing a metal component which is a metal of Groups IVB, VB and VIB, and the non-noble metals of Group VIII, in any of the forms described above, in association or combination with an organo-nitrogen compound or an organo-phosphorus compound wherein the nitrogen and the phosphorus are trivalent.

The organic promoter can, in its broader sense, be any organo-nitrogen or organo-phosphorus compound wherein the nitrogen and phosphorus are trivalent. Preferably, however, the organo-nitrogen promoter is an amine, especially a tertiary amine of the formula

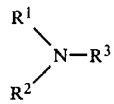

wherein $R^1$, $R^2$ and $R^3$ are the same or different and are alkyl, cycloalkyl, aryl or acyl groups which may be substituted by non-interfering groups, preferably having up to 20 carbon atoms, such as trimethylamine, triethylamine, triphenylamine, ethylenediamine tetraacetic acid, and the like, or a heterocyclic amine such as pyridine, picoline, quinoline, methylquinoline, hydroxy quinoline, pyrrole, pyrrolidine, and the like, or an imidazole, such as imidazole, methyl imidazole and the like, or an imide of a carboxylic acid which may be monobasic or polybasic and which may be aliphatic or aromatic and preferably contains up to 20 carbon atoms, such as acetic acid, succinic acid, phthalic acid, pyromellitic acid, e.g., N,N-dimethylacetamide, succinimide phthalimide and pyromellitic diimide, or a nitrile or amide which may be aliphatic or aromatic and preferably contain up to 20 carbon atoms, e.g., acetonitrile, hexamethyl phosphoric triamide, and like imides, nitriles, and amides, or an oxime such as cyclohexanone oxime, and the like. It will be understood, however, that higher molecular weight promoters, e.g., polymeric forms of the organo-nitrogen compounds, may be used such as polyvinylpyridine, polyvinyl pyrrolidone, and the like.

The organo-phosphorus promoter is preferably a phosphine of the formula

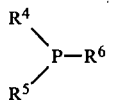

wherein $R^4$, $R^5$ and $R^6$ may be the same or different and are alkyl, cycloalkyl, aryl groups, amide groups or halogen atoms, preferably containing 1 to 20 carbon atoms in the case of alkyl and cycloalkyl groups and 6 to 18 carbon atoms in the case of aryl groups. Typical phosphines include trimethylphosphine, tripropylphosphine, tributyl phosphine, tricyclohexyphosphine and triphenylphosphine.

Although, preferably the organic promoters are added separately to the catalyst system, it is possible to add them as complexes with the Group VIII noble metal such as the trichloro trispyridine rhodium, tris(-triphenyl phosphine)rhodium, chlorotris(triphenyl phosphine)rhodium, and chlorocarbonyl bis (triphenyl phosphine) rhodium, and like complexes. Both free organic promoters and complexed promoters can also be used. Indeed, when a complex of the organic promoter and the Group VIII noble metal is used, it is desirable to add free organic promoter as well. The amount of organic promoter will generally lie in the ranges referred to above for the metal promoter except that preferably up to 50 mols per mol of catalyst are employed.

The ratio of ester to the halide in the reaction system can vary over a wide range. Typically, there are used 1 to 500 equivalent of halide, preferably 1 to 200 equivalents per equivalent. Thus, there are typically used 1 to 500 mols, preferably 1 to 200 mols of ester per mol of halide reactant. By maintaining the partial pressure of carbon monoxide at the values specified, adequate amounts of the reactant are always present to react with the hydrocarbyl halide. The carbonylation step is readily carried out in a single reaction zone to which a halide source, e.g., a hydrocarbyl halide such as methyl iodide, and the methyl acetate are both charged and are heated together, preferably in the liquid phase, in the presence of carbon monoxide and in the presence of the Group VIII metal catalyst. It will be understood that the hydrocarbyl halide may be formed in situ and the halide may thus be supplied to the system not only as the hydrocarbyl halide but the halogen moiety may also be supplied as another organic halide or as the hydrohalide or other inorganic halide, e.g., salts, such as the alkali metal or other metal salts, or even as elemental iodine or bromine.

As previously mentioned, in carrying out the carbonylation steps described above, a wide range of temperatures, e.g., 20° to 500° C. are suitable but temperatures of 100° to 300° C. are preferably employed and the more preferred temperatures generally lie in the range of 125° to 250° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but excessively high pressures, which require special high-pressure equipment, are not necessary. In general, the reaction is effectively carried out by employing a carbon monoxide partial pressure which is preferably 5 to 2,000 psi, although carbon monoxide partial pressures of 0.1 to 15,000 psi can also be employed. The total pressure is that required to provide the desired CO partial pressure and preferably that required to maintain the liquid phase. Typically, total pressures up to about 3,000 psig are used but most preferably they are at most about 1,000 psig. The reaction can be advantageously carried out in an autoclave or similar apparatus.

As previously mentioned, the process of this invention is also applicable to gaseous streams obtained from the carbonylation of methyl acetate or dimethyl ether with Group VIII noble metals, especially rhodium and/or palladium catalysts with carbon monoxide and hydrogen in the presence of a halide moiety, especially an iodine moiety for the preparation, in addition to acetic anhydride, of ethylidene diacetate, acetaldehyde and acetic acid, as described in the above-mentioned Belgian Pat. No. 839,321 which is the counter-part of U.S. application Ser. No. 654,662 filed Feb. 5, 1976. Such carbonylation of methyl acetate is carried out as described above except that significant amounts of hydrogen are included with the carbon monoxide. The partial pressure of hydrogen employed falls within the above specified ranges for carbon monoxide partial pressure. Molar ratios of carbon monoxide to hydrogen, broadly within the range of 1:100 to 100:1, desirably within the range of 50:1 to 1:50, and preferably within the range of 10:1 to 1:10 can be employed. Molar ratios of carbon monoxide to hydrogen within the range of 0.1:5 to 5:1 are especially preferred.

It will be apparent that the carbonylations referred to above are carried out under substantially anhydrous conditions. The presence of minor amounts of water, however, such as may be found in commercially available reactants, is permissible. Normally, however, the presence of more than 5 mol % of water in any one or more of the reactants should be avoided, the presence of less than 3 mol % of water desired, and the presence of less than 1 mol % is preferred.

The following examples of specific application will serve to provide a fuller understanding of the invention but it will be understood that these examples are given for illustrative purposes only, however, and are not to be interpreted as limitative of the invention. In the examples, all parts are molar unless otherwise indicated.

EXAMPLE I

A carbonylation zone in the form of a stirred pressure reactor provided with a liquid overflow withdrawal line is filled to the level of the withdrawal line, and connected to a system such as illustrated in the drawing, with a mixture composed of approximately 93.5 mol percent methyl acetate, 2.25 mol percent methyl iodide, 4 mol percent lithium iodide and 0.25 mol percent rhodium acetate. This mixture is heated to about 170° C. and carbon monoxide is introduced into the reactor to provide and maintain a partial pressure of carbon monoxide of about 300 psi. Continuous liquid feed to the reactor is then begun and liquid reaction product is continuously withdrawn. The reaction is carried out to provide a residence time in the reactor of about three hours. Thus, there are continuously fed approximately 750 parts per hour of methyl acetate (including 490 parts recycle methyl acetate) along with recycle of the iodine, lithium and rhodium values representing 38 parts per hour of methyl iodide, 32 parts per hour of lithium iodide and 2 parts per hour of rhodium acetate, together with recycle acetic anhydride, the recycle streams being obtained as described below. The reaction mixture is continuously withdrawn at the rate of 1,000 parts per hour and is first flashed at about 80 psia and 150° C. The heavy liquid from the flash, which contains the catalyst components, methyl acetate and acetic anhydride is recycled to the carbonylation zone at the rate of approximately 300 parts per hour. The vapor from the flash distillation is then distilled to separate light components including methyl acetate and methyl iodide for recycle. The bottoms from this distillation are comprised of approximately 260 parts per hour of product acetic anhydride. A non-condensible gas stream which contains valuable iodine values is withdrawn as a purge stream from the upper portion of the reactor and is cooled and flashed in zone 10 to separate substantially all of the condensible components for recycle to the reactor. The vapor from this flash is compressed in a compressor 20 to 500 paig and fed to a tray scrubber zone 30 having 10 theoretical plates where it is brought into counter-current contact with a stream of some of the product acetic anhydride introduced at the rate of 30 parts per hour. This counter-current contact removes 99.9+% of the iodine values contained in the gaseous stream. The iodine-enriched acetic anhydride stream is added to the recycle streams to the carbonylation reactor and provides some of the acetic anhydride and iodine component of the carbonylation recycle.

EXAMPLE II

Example I is repeated and the treated non-condensible gas stream recovered from scrubber zone 30 is passed upwardly through a scrubber zone 32 also having 10 theoretical plates where it is brought into counter-current contact with a stream of saturated aqueous potassium hydroxide (40 mol per hour) introduced at a temperature of about 80° C. The gaseous effluent from this second scrubber zone contains less than 2 ppm of iodine values. The potassium hydroxide stream is withdrawn from the lower portion of zone 32 and is recycled to the upper portion of the zone for contact with further quantities of the gaseous stream issuing from zone 30. The recycling potassium hydroxide stream is occasionally purged and replenished to prevent the build-up of iodine compounds.

EXAMPLE III

Using a reactor in the form of a stirred autoclave (constructed of Hastelloy C), provided with an inlet for liquid, a line connected to a source of carbon monoxide and hydrogen, and recycle gas, methyl acetate is carbonylated in the presence of a catalyst composed of rhodium trichloride trihydrate, tributyl phosphine and chromium hexacarbonyl, as follows. The reactor is charged with a mixture of approximately 20 percent methyl iodide and 80 percent methyl acetate containing approximately 0.007 mol (expressed as Rh) of rhodium trichloride trihydrate, 0.118 mol of tributyl phosphine and 0.007 mol (expressed as Cr) of chromium hexacarbonyl, and then heated for one hour at 160° C. Continuous operation is then begun with a feed, including recycle streams, of about 510 parts per hour methyl iodide and about 2560 parts per hour methyl acetate. Carbon monoxide is supplied to the reactor to maintain partial pressure of 420 psi and similarly hydrogen is supplied to maintain a hydrogen partial pressure of 55 psi. The reaction product effluent is removed continuously from the reaction zone in the vapor state, condensed and collected at the rate of about 1900 parts per hour of condensate. The non-condensed portion of the effluent which includes some methyl acetate and methyl iodide is recycled and combined with make-up methyl acetate, methyl iodide, as well as make-up carbon monoxide and hydrogen and the above-indicated partial pressures are maintained.

The above-mentioned condensate is then passed into a zone of reduced pressure of about 90 psia where dissolved gases contained in the condensate are released amounting to about 60 parts per hour along with 35 parts per hour of methyl acetate and 6 parts per hour of methyl iodide. The liquid from this lower pressure zone which contains the bulk of the methyl acetate and methyl iodide and the produce acetic anhydride from the carbonylation reactor is then distilled as described in Example I to separate the methyl acetate and methyl iodide for recycle to the reactor and to produce the product acetic anhydride. The above-mentioned dissolved gas stream is compressed and passed into a separation zone 10 maintained at 500 psia and 50° C. wherein most of the methyl acetate and methyl iodide are condensed and provide a liquid stream for recycle to the carbonylation reactor. The non-condensible stream from zone 10 which contains about 60 parts per hour of non-condensible gases along with 1.5 parts per hour of methyl acetate and 0.3 parts per hour of iodine values is then supplied to a tray scrubber zone as described in Example I and treated counter-currently with acetic anhydride introduced at the rate of 40 parts per hour. As in Example I, this counter-current contact removes 99.9+% of the iodine values contained in the gaseous stream. The iodine-enriched acetic anhydride stream from zone 30 is suitably added to the liquid stream from the reduced pressure separation zone preceding zone 10 where the acetic anhydride will be separated from the iodine values which can be recycled to the carbonylation reactor.

EXAMPLE IV

Example II is repeated except that the treated gaseous stream from zone 30 in Example III is used as the feed. Again, a gas stream containing less than 2 ppm of iodine values is obtained.

What is claimed is:

1. A process for the recovery of halogen values from an effluent gas stream obtained in the carbonylation of methyl acetate and/or methyl ether in the presence of a Group VIII metal and a halogen moiety which comprises bringing said gas stream into counter-current contact in a scrubbing zone with at least one of the products of the carbonylation reaction having a boiling point above 100° C.

2. A process as defined in claim 1, wherein the carbonylation produces acetic anhydride and said acetic anhydride is brought into counter-current contact in said gaseous stream in said scrubbing zone.

3. A process as defined in claim 1, wherein the carbonylation produces ethylidene diacetate and said ethylidene diacetate is brought into counter-current contact in said gaseous stream in said scrubbing zone.

4. A process as defined in claim 1, wherein the carbonylation produces acetic acid and said acetic acid is brought into counter-current contact in said gaseous stream in said scrubbing zone.

5. A process as defined in claim 1, wherein the gaseous stream after passing through said scrubbing zone is subjected to a final treatment to remove residual or trace amounts of said halogen values.

* * * * *